United States Patent [19]
Young et al.

[11] Patent Number: 5,449,850
[45] Date of Patent: Sep. 12, 1995

[54] PROCESS FOR OLIGOMERIZING $C_3$ AND HIGHER OLEFINS USING ZIRCONIUM ADDUCTS AS CATALYSTS (CS-467)

[75] Inventors: David A. Young; Larry O. Jones, both of Baton Rouge, La.; Troy J. Campione, Houston, Tex.

[73] Assignee: Exxon Chemical Patents Inc., Linden, N.J.

[21] Appl. No.: 668,009

[22] Filed: Mar. 12, 1991

[51] Int. Cl.$^6$ ................................................ C07C 2/26
[52] U.S. Cl. ..................................... 585/523; 585/512
[58] Field of Search .......................... 585/523, 572

[56] References Cited

U.S. PATENT DOCUMENTS

| | | | |
|---|---|---|---|
| 3,622,552 | 11/1971 | Fukuda et al. | 526/142 |
| 4,361,714 | 11/1982 | Langer et al. | 585/521 |
| 4,377,720 | 3/1983 | Langer | 585/527 |
| 4,396,788 | 8/1983 | Langer, Jr. | 585/523 |
| 4,409,409 | 10/1983 | Langer, Jr. et al. | 585/255 |
| 4,410,750 | 10/1983 | Langer, Jr. | 585/521 |
| 4,434,312 | 2/1984 | Langer, Jr. | 585/523 |
| 4,434,313 | 2/1984 | Langer, Jr. | 585/527 |
| 4,442,309 | 4/1984 | Langer, Jr. | 585/523 |
| 4,486,615 | 12/1984 | Langer, Jr. | 585/523 |
| 4,855,525 | 8/1989 | Young et al. | 585/523 |
| 4,855,525 | 8/1989 | Young et al. | 585/523 |

FOREIGN PATENT DOCUMENTS 62-000430  1/1987  Japan.

*Primary Examiner*—P. Achutamurthy
*Attorney, Agent, or Firm*—Richard D. Jordan

[57] ABSTRACT

$C_3$ and higher olefins are oligomerized using a two component catalyst system comprising (a) a soluble adduct of zirconium tetrahalide, the halogen being Br or Cl, with an organic compound selected from the group of esters, ketones, ethers, amines, nitriles, anhydrides, acid chlorides, amides or aldehydes, the organic compound having up to about 30 carbon atoms and (b) an alkyl metal selected from the group $R_2AlX$, $RAlX_2$, $R_3Al_2X_3$, $R_3Al$ and $R_2Zn$ where R is $C_1$–$C_{20}$ alkyl and X is Cl or Br. $ZrCl_4$ adducts with organic acetates are the preferred embodiments. Dimers, trimers and tetramers are selectively prepared in the process.

19 Claims, No Drawings

PROCESS FOR OLIGOMERIZING C3 AND HIGHER OLEFINS USING ZIRCONIUM ADDUCTS AS CATALYSTS (CS-467)

This invention relates to an improved process for oligomerizing $C_3$ and higher olefins. More particularly, this invention relates to the production of such oligomers of higher olefins utilizing an adduct of zirconium tetrahalides as an essential part of the homogeneous catalyst system.

The oligomerization of ethylene to produce linear alpha-olefins is generally known in the art. The use of zirconium-containing catalysts is disclosed, for example, in U.S. Pat. Nos. 4,486,615; 4,442,309; 4,434,313; 4,434,312; 4,410,750; 4,409,409; 4,396,788; 4,377,720 and 4,361,714. A number of these patents disclose reaction products of zirconium halides to provide zirconium alkoxides or carboxylates, such as U.S. Pat. Nos. 4,409,409 and 4,486,615 which show various derivatives of tetravalent zirconium. The concept of the present invention, use of zirconium tetrahalide (bromide, chloride or mixtures thereof) adducts of certain organic compounds, preferably certain alkyl acetate esters, as a catalyst for oligomerization of $C_3$ and higher olefins, is not disclosed by these references.

Japanese Application 60-137683, filed Jun. 25, 1985 by Shiroki et al. and published Jan. 6, 1987 as Japanese Kokai 62-000430, discloses the production of linear alpha-olefins by polymerizing ethylene in the presence of a mixture consisting of a zirconium halide, an alkyl aluminum halide and a compound which may be that of sulfur or that of nitrogen. The catalyst is described as a three component catalyst.

U.S. Pat. No. 3,622,552, issued Nov. 23, 1971 to Fukuda et al. discloses the preparation of crystalline homo- or co-polymers of olefin using a three component catalyst comprising (1) an organoaluminum compound of the formula $AlR_2X$, R being a hydrocarbyl, X being halogen, (2) a Group IV, V or VI transition metal halide and (3) a saturated or unsaturated carboxylic ester having a side chain on a carbon atom in alpha position to ester carbon atoms. Fukuda et al. do not disclose the preparation of linear alpha-olefin oligomers and do not disclose the formation of a homogeneous two component catalyst, one component of which being an adduct of zirconium tetrahalide with an organic compound.

U.S. Pat. No. 4,855,525, issued Aug. 8, 1989, to the inventors hereof, discloses the use of zirconium tetrahalide adducts as catalysts for the production of linear alpha-olefins from ethylene. The present invention is based on the discovery that the same zirconium halide adduct catalyst system may be effectively used to oligomerize other olefins, namely $C_3$ and higher olefins.

The present invention is concerned with a process comprising the use of homogeneous catalyst system for conducting the oligomerization of propylene and higher olefins. In the present invention the objective is toward the production of dimers, trimers or tetramers of the olefins and not the production of high molecular weight, crystalline polymers.

The present invention provides a number of desirable advantages: the catalyst is readily prepared and is soluble, it may be used in high concentrations, it is storage stable and use of the novel adduct catalyst system provides principally branched products with suitable conversions of $C_3$ and higher olefins. The solubility of the novel catalyst of this invention enables the catalyst to be fed to the reaction vessel in an easily controlled liquid stream. Importantly the catalyst exhibits complete solution into the reaction solution and all the zirconium is available for catalysis in contrast to prior art techniques wherein zirconium was added as a partially soluble salt.

In accordance with the present invention there has been discovered a process for oligomerizing $C_3$ and higher olefins in the presence of a homogeneous two component catalyst, the first component being an adduct of $ZrCl_aBr_b$, where $a+b=4$ and a or b may be 0, 1, 2, 3 or 4, with an organic compound selected from the group consisting of esters, ketones, ethers, amines, nitriles, anhydrides, acid chlorides, amides or aldehydes, said organic compound having up to 30 carbon atoms, and the second component being an alkyl metal catalyst selected from the group consisting of $R_2AlX$, $RAlX_2$, $R_3Al_2X_3$, $R_3Al$ and $R_2Zn$ wherein R is $C_1$-$C_{20}$ alkyl and X is Cl or Br, the oligomerization being conducted in a reactor vessel at 50° C. to 300° C. at a suitable pressure (depending on the olefin used) of about 15 to 5,000 psig in the liquid phase.

Suitable olefins which may be oligomerized in accordance with the present invention include those having about 3 to 20 carbon atoms, such as propylene, butylene, hexene, decene, tetradecene and the like, including both linear and branched olefins. Particularly preferred are aliphatic, monounsaturated linear hydrocarbyl unsubstituted 1-olefins such as propylene-1, butene-1, hexene-1, decene-1, and tetradecene-1 which have about 3 to 20 carbon atoms. The invention is also considered applicable to aromatic or cycloaliphatic olefins capable of being oligomerized such as styrene, 4-vinlycyclohexene and dicyclopentadiene.

The products of this invention have a number of uses. They are particularly useful as feedstocks for hydroformylation and hydrogenation in order to prepare high molecular weight alcohols having a specific molecular weight. Such alcohols are used for preparation of plasticizers and surfactants and detergents. For example, 1-decene may be dimerized to $C_{20}$ olefin which may be hydroformylated and hydrogenated to prepare a $C_{21}$ alcohol, which may be ethoylated to provide a useful surfactant. Also, 1-decene may be trimerized and tetramerized to make $C_{30}/C_{40}$ olefins which may then be hydrogenated to make synthetic basestocks for lubricants.

An essential aspect of the present invention is that the first component of the catalyst is an adduct of zirconium tetrahalide, the halogen being Br or Cl or a mixture of said halides, with certain organic compounds. The second component of the catalyst, which is an alkyl aluminum or alkyl zinc compound, is well known in the art and has been used conventionally in ethylene oligomerization processes as a co-catalyst component.

The first component of the catalyst may be an adduct of $ZrCl_aBr_b$ with an ester, a ketone, an ether, an amine, a nitrile, an anhydride, an acid chloride an amide or an aldehyde and these various adduct-forming organic components may have up to about 30 carbon atoms. The adducts generally include mole ratios of organic component to zirconium of from about 0.9 to 1 up to about 2 to 1. Preferred are equimolar adducts. The adduct must be soluble in and stable in the solvent which is used as the reaction medium for the oligomerization process of the present invention.

Adducts may be formed from $ZrCl_4$, $ZrBr_4$, as well as the mixed tetrahalides: $ZrClBr_3$, $ZrCl_2Br_2$ and $ZrCl_3Br$, wherein the halogen is limited to Cl or Br. $ZrCl_4$ adducts are especially preferred.

Preferred are adducts of $ZrCl_4$ with esters of the general formula $R_1COOR_2$ where $R_1$ and $R_2$ may be alkyl, aryl, alkaryl or aralkyl groups having a total of 1 to 30 carbon atoms and $R_1$ may also be hydrogen. $R_1$ and $R_2$ taken together may also represent a cycloaliphatic group and the ester may be compounds such as gammabutyrolactone or phthalide. Especially preferred are alkyl acetate esters where the alkyl group has 6 to 16 carbon atoms such as n-hexyl acetate, n-heptyl acetate, n-octyl acetate, n-nonyl acetate, n-decyl acetate, isohexyl acetate, isodecyl acetate, and the like which have been found to form discrete dimeric equimolar adducts with $ZrCl_4$. This particularly preferred embodiment may be represented by the formula $(ZrCl_4 \cdot CH3COOR_1)_2$ where $R_1$ is a $C_6$ to $C_{16}$ alkyl or a mixture of $C_6$ to $C_{16}$ alkyls. These preferred ester adducts are capable of providing highly concentrated solutions in the solvent used as the reaction solvent, i.e., up to about 40% by weight of $ZrCl_4$, when preferred mixed isomers of isodecyl acetate esters are used. Particularly useful are mixtures of various isomers of isohexyl, isoheptyl, isooctyl, isononyl, isodecyl or isotridecyl acetate sold by Exxon Chemical Company, respectively, as Exxate® 600, Exxate® 700, Exxate® 800, Exxate® 900, Exxate® 1000 and Exxate® 1300. The isohexyl acetate mixture comprises about, by weight, 36–38% n-hexyl acetate, 18–20% 2-methyl-1-pentyl acetate, 22–24% 3-methyl-1-pentyl acetate and 16–18% 4-methyl-1-pentyl acetate as principal compounds. Exxate® 1000 isodecyl acetate mixture is a complex mixture of isomers and gas chromatographic analysis shows about 100 different isomers being present, none of which are greater than about 12% by weight of the mixture. Exxate® 1000 has a boiling point range of about 425° F. to 482° F. (95% distilled).

These adducts have been prepared by simple addition of the organic ester to a slurry of $ZrCl_4$ in the inert organic or alpha-olefin solvent. The ester is added slowly to the stirred mixture at room temperature and complete formation and dissolution of the adduct is observed after several minutes. The dissolution is exothermic and the mixture reaches a temperature of about 50° C. as a result of the heat of reaction due to adduct formation.

Also suitable, for providing soluble zirconium adducts useful as the first component catalyst of the present invention are ketones, ethers and aldehydes which may be represented, respectively, by the formulas: $R_1C(:O)R_2$, $R_1OR_2$ and $R_1C(:O)H$ where $R_1$ and $R_2$ represent alkyl, aryl, alkaryl or aralkyl groups, the total of $R_1$ and $R_2$ being not more than about 30 carbon atoms. Also suitable are primary, secondary and tertiary amines wherein the hydrocarbyl radicals have up to about 30 carbon atoms, such as n-dodecyl amine and tri-n-hexyl amine. Also suitable are hydrocarbyl cycloaliphatic ethers and ketones having from 4 to 16 carbon atoms, e.g., cyclohexanone.

Other adduct-forming organic compounds useful in the present invention include nitriles, anhydrides, acid chlorides and amides having up to 30 carbon atoms. These may be represented, respectively, by the formulas $RC\equiv N$, $(R(C:O))_2O$ $RC(:O)Cl$ and $RC(:O)NH_2$, $RC(:O)NHR$ or $RC(:O)NR_2$ where R represents a hydrocarbyl alkyl, aryl, alkaryl or an aralkyl group having up to about 30 carbon atoms. Examples are adducts of $ZrCl_4$ with n-undecane nitrile, n-decyl succinic anhydride and n-decanoyl chloride.

The second catalyst component of the present invention is an aluminum alkyl of the formulas $R_2AlX$, $RAlX_2$, $R_3Al_3X_3$, $R_3Al$ or a zinc alkyl of the formula $R_2Zn$, where $R_1$, $R_2$ and $R_3$ may be $C_1$–$C_{20}$ alkyl and X is Cl or Br. Diethylaluminum chloride, aluminum ethyl dichloride and mixtures thereof are preferred.

The process of the present invention is conducted under generally conventional oligomerization conditions of temperature and pressure, that is, about 50° C. to 250° C. and about 500–5000 psig, preferably 1000 to 3500 psig for $C_3$ to about $C_6$ olefins, about 15–5000 psig for $C_7$ and higher olefins. Pressure is widely variable because of the differences in the olefin vapor pressures at reaction temperatures.

The process is conducted in the liquid phase. When $C_3$ and $C_4$ olefins are being oligomerized, there is employed an inert solvent which must be non-reactive with the catalyst system or in the presence of a solvent such as a liquid alpha-olefin, particularly $C_6$–$C_{100}$ alpha-olefins. Other suitable solvents for both olefin and catalyst include aromatic or aliphatic hydrocarbons and halogenated aromatics such as chlorobenzene, dichlorobenzene and chlorotoluene. Preferred solvents are toluene, xylenes, particularly p-xylene, and $C_3$–$C_{24}$ alkanes, especially n-heptane and n-decane. Mixtures of these solvents may also be used. Generally speaking, for $C_5$ and higher olefins the vapor pressure of the olefin is usually suitable so that a liquid phase reaction mixture may be maintained without the need for a solvent for the olefin reactant, but a solvent is required to act as a carrier for introduction of the catalyst into the reactor.

The amount of first catalyst component used in conducting oligomerization according to the present invention may be expressed as about $2 \times 10^{-6}$ moles to about $200 \times 10^{-6}$ moles of zirconium adduct catalyst component per gram of olefin being oligomerized. The second catalyst component, such as diethylaluminum chloride, is used in an amount such that the molar ratio of second component to first component is from about 15:1 to about 3:1.

The preferred temperature range to obtain oligomerization is about 120° C. to 250° C. At these preferred temperatures, the pressure should be about 1000 psig in a continuous stirred tank reactor, which will produce about 10–65% conversion of olefins to dimers, trimers and tetramers for $C_3$ to $C_6$ olefins, and about 15 to 5000 psig for $C_7$ or higher olefins.

In practicing the process of the present invention, the presence of water in the system should be minimized, since the catalyst of this invention is particularly sensitive to the presence of water. It has been found that only minor amounts of water will tend to produce undesirable quantities of high molecular weight polyolefins and will reduce conversions to the desired product. The amounts of water are best controlled with respect to the molar ratio of zirconium to water in the reaction mixture. The amount of water present is preferably in the range of about 20 to 1 to about 5,000 to 1 moles of zirconium per mole of water or higher. Within these desired ranges the percentage of high molecular weight (greater than 10,000) polyolefins is between 0.017 and 0.04 wt. %, based on the weight of product with conversions to product being in the range of about 55 to 70%. However, at $Zr/H_2O$ mole ratios of 5 to 10 to 1 or less, while a conversion to desired oligomer product will occur, substantial amounts of polyolefins may be formed and reactor fouling might occur. The maximum amount of water from a practical viewpoint is considered to be a Zr/H$_2$O mole ratio of at least 10 to 1.

The process of the present invention will provide primarily oligomers which are dimers, trimers and tetramers of the olefin feedstock which is subjected to the process. Generally, the conversion of olefin to oligomers will be on the order of about 30 to 60% with the products comprising about 35 to 70% dimers, 10–20% trimers, 5–20% tetramers with typically 5% or less of higher molecular weight oligomers and polymeric materials. For example, hexadecene-1 may be selectively converted to oligomers comprised of about 80% dimer (C$_{32}$ olefin) and 20% trimer (C$_{48}$ olefin) with only trace amounts of other products. Thus, the present invention provides an advantageous method of preparing commercially acceptable yields of olefins having specific molecular weight values.

The invention is further illustrated by the following Examples which are not to be considered as limitative of its scope.

The oligomerizations in the Examples below were conducted in a 1-liter stirred autoclave. Reactor volume was controlled at about 500 cc by a dip leg which served as the reactor exit. The autoclave was electrically heated and oil cooled. The moisture content was monitored continuously using aluminum oxide sensors. Olefin was fed continuously at a measured rate to the reactor during the test runs. Reaction solvent was dried over sieves to less than 1 ppmw and then metered continuously into the reactor. Catalyst and co-catalyst solutions were prepared in a dry box using heated and evacuated glassware to insure minimum water contamination. The zirconium catalyst was diluted in dry solvent (solvent dried to less than 1 ppmw over molecular sieves) to a concentration of about $20 \times 10^{-6}$ gram moles of zirconium per gram of solution. The solutions were then transferred to the reactor feed tanks and held under a nitrogen blanket. The aluminum co-catalyst solutions were prepared from 20% by weight stock solutions obtained from a supplier. Again, dilution solvent was dried to less than 1 ppm water content before using. Co-catalyst was generally diluted to about $200 \times 10^{-6}$ gram moles of aluminum per gram of solution.

EXAMPLE 1

Zirconium tetrachloride powder 80.0 g, 0.343 mole, was placed in a dry glass vessel under a dry argon atmosphere. Next 125.0 g of dry n-heptane solvent was added. The resulting slurry was stirred while dry isodecyl acetate (mixed isomers sold as Exxate ® 1000 by Exxon Chemical Company), 70.0 g, 0.318 mole, was added dropwise over 10 minutes. There was an exotherm to about 45° C. while the ZrCl$_4$ dissolved producing a hazy, pale yellow solution. The haze was due to a very small amount of inorganic impurities and unreacted ZrCl$_4$. This was filtered through a dry medium porosity glass fritt under argon and the fritt rinsed with 7.2 g dry heptane. The combined rinse and filtrate weighed 282.2 g and consisted of a clear, pale yellow solution that contained 28.3 wt. % ZrCl$_4$, in the form of a soluble complex with the isodecyl acetate.

EXAMPLE 2

Using the ZrCl$_4$ adduct prepared above in Example 1 and diethylaluminum chloride (DEAC) co-catalyst, a series of oligomerizations of propylene were carried out using the conditions set forth in Table 1 below; the results are set forth in Table 2.

EXAMPLE 3

Similar oligomerizations were carried out using 1-decene as the feedstock. The conditions are shown in Table 3 and the results in Table 4.

EXAMPLE 4

Similar oligomerization was carried out using 1-tetradecene as the olefin. Conditions are shown in Table 5 and results in Table 6.

EXAMPLES 5

The process was repeated using 1-hexadecene as the olefin. Conditions are shown in Table 7 and results in Table 8.

TABLE 1

| Variable | REACTION CONDITIONS | | | |
|---|---|---|---|---|
| | Run 1 | Run 2 | Run 3 | Run 4 |
| Temperature | 150 deg. C. | 150 deg. C. | 150 deg. C. | 150 deg. C. |
| Pressure$^{(a)}$ | 1000 psig | 1000 psig | 1000 psig | 1000 psig |
| Propylene Feed | 315 g/hr | 315 g/hr | 310 g/hr | 410 g/hr |
| Solvent p-Xylene Feed | 620 g/hr | 620 g/hr | 515 g/hr | 275 g/hr |
| DEAC Conc. $\times 10^{-6}$ moles/g | 269.1 | 269.1 | 269.1 | 269.1 |
| DEAC Flow Rate | 53.3 cc/hr | 53.3 cc/hr | 79.0 cc/hr | 36.4 cc/hr |
| Zr Adduct Conc. $\times 10^{-6}$ moles/g | 25.3 | 25.3 | 25.3 | 25.3 |
| Zr Adduct Flow Rate | 41.9 cc/hr | 41.9 cc/hr | 62.4 cc/hr | 65.5 cc/hr |
| Al/Zr Molar Ratio | 13.5 | 13.5 | 13.5 | 5.9 |
| Residence Time | 17 min | 4 hr | 1 hr | 1 hr |

$^{(a)}$The pressure was adjusted to the indicated value by the addition of dry nitrogen gas.

TABLE 2

| | RESULTS | | | |
|---|---|---|---|---|
| Item | Run 1 | Run 2 | Run 3 | Run 4 |
| Productivity, g Product/g Zr | 1450 | 2450 | 260 | 1720 |
| Conversion | 38.8% | 65.5% | 10.5% | 52.6% |
| Product Distribution: | | | | |
| C6 | 67.3% | 71.0% | 66.5% | 38.5% |
| C9 estimates | 21.9% | 20.0% | 25.4% | 28.2% |
| C12 | 8.5% | 6.2% | 6.6% | 18.9% |
| C15 | 2.2% | 1.4% | 1.2% | 5.8% |
| C18 | n.a. | trace | 0.2% | 6.4% |
| C21 | n.a. | trace | trace | 1.0% |
| Isomer Distribution For The Most Abundant Hexenes: | | | | |
| 1. 2-methyl-1-pentene | 75.5% | 78.6% | 71.0% | 54.6% |
| 2. unidentified | 9.8% | 7.8% | 6.6% | 14.8% |
| 3. unidentified | 6.8% | 5.5% | 5.1% | 12.3% |
| 4. unidentified | 2.3% | 3.8% | 5.1% | 11.5% |
| 5. unidentified | 1.8% | 1.3% | 3.9% | 1.2% |
| 6. unidentified | 1.3% | 1.2% | 1.7% | 1.2% |

TABLE 3
REACTION CONDITIONS

| Variable | Run 1 | Run 2 |
| --- | --- | --- |
| Temperature | 150 deg. C. | 130 deg. C. |
| Pressure[a] | 1000 psig | 1000 psig |
| 1-Decene Feed | 400 g/hr | 400 g/hr |
| DEAC Conc. $\times 10^{-6}$ moles/g | 211.3 | 211.3 |
| DEAC Flow Rate | 41.1 cc/hr | 41.1 cc/hr |
| Zr Adduct Conc. $\times 10^{-6}$ moles/g | 38.3 | 38.3 |
| Zr Adduct Flow Rate | 37.6 cc/hr | 37.6 cc/hr |
| Al/Zr Molar Ratio | 5.5 | 5.5 |
| Residence Time | 45 min | 45 min |

[a]The pressure was adjusted to the indicated value by addition of dry nitrogen gas.

TABLE 4
RESULTS

| Item | Run 1 | Run 2 |
| --- | --- | --- |
| Productivity, g Product/g Zr | 2014 | 1766 |
| Conversion | 58.4% | 51.2% |
| Product Distribution | | |
| C20 | 73.3% | 69.8% |
| C30 | 20.5% | 23.2% |
| C40 | 6.1% | 7.0% |
| Isomer Distribution For The Most Abundant C20 Olefins | | |
| 1. unidentified | 63.9% | 65.3% |
| 2. unidentified | 17.9% | 17.2% |
| 3. unidentified | 8.7% | 8.6% |
| 4. unidentified | 6.8% | 5.2% |
| 5. unidentified | 0.8% | 1.0% |

TABLE 5
REACTION CONDITIONS

| Variable | Run 1 |
| --- | --- |
| Temperature | 150 deg. C. |
| Pressure[a] | 1000 psig |
| 1-Tetradecene Feed | 470 g/hr |
| DEAC Conc. $\times 10^{-6}$ moles/g | 289.4 |
| DEAC Flow Rate | 30.1 cc/hr |
| Zr Adduct Conc. $\times 10^{-6}$ moles/g | 40.9 |
| Zr Adduct Flow Rate | 34.2 cc/hr |
| Al/Zr Molar Ratio | 6.2 |
| Residence Time | 45 min |

[a]The pressure was adjusted to the indicated value by the addition of dry nitrogen gas.

TABLE 6
RESULTS

| Item | Run 1 |
| --- | --- |
| Productivity, g Product/g Zr | 2372 |
| Conversion | 56.7% |
| Product Distribution | |
| C28 | 83.5% |
| C42 | 16.5% |
| Isomer Distribution For The Most Abundant C28 Olefins | |
| 1. unidentified | 65.7% |
| 2. unidentified | 15.1% |
| 3. unidentified | 7.9% |
| 4. unidentified | 4.7% |
| 5. unidentified | 1.2% |

TABLE 7
REACTION CONDITIONS

| Variable | Run 1 |
| --- | --- |
| Temperature | 150 deg. C. |
| Pressure[a] | 1000 psig |
| 1-Hexadecene Feed | 535 g/hr |
| DEAC Conc. $\times 10^{-6}$ moles/g | 287.0 |
| DEAC Flow Rate | 30.6 cc/hr |
| Zr Adduct Conc. $\times 10^{-6}$ moles/g | 42.2 |
| Zr Adduct Flow Rate | 33.5 cc/hr |
| Al/Zr Molar Ratio | 6.2 |
| Residence Time | 1 hr |

[a]The pressure was adjusted to the indicated value by the addition of dry nitrogen gas.

TABLE 8
RESULTS

| Item | Run 1 |
| --- | --- |
| Productivity, g Product/g Zr | 2803 |
| Conversion | 58.7% |
| Product Distribution | |
| C32 | 80.0% |
| C48 | 20.0% |
| Isomer Distribution For The Most Abundant C32 Olefins | |
| 1. unidentified | 64.2% |
| 2. unidentified | 15.7% |
| 3. unidentified | 7.7% |
| 4. unidentified | 5.1% |
| 5. unidentified | 1.7% |

What is claimed is:

1. A process for conducting the oligomerization of $C_3$ and higher olefins which comprises oligomerizing said olefins in the presence of a homogeneous two component catalyst, the first component being an adduct of $ZrCl_aBr_b$, where $a+b=4$ and a or b may be 0, 1, 2, 3 or 4, with an organic compound selected from the group consisting of esters, ketones, ethers, amines, nitriles, anhydrides, acid chlorides, amides or aldehydes, said organic compound having up to 30 carbon atoms and the second component being an alkyl metal catalyst selected from the group consisting of $R_2AlX$, $RAlX_2$, $R_3Al_2X_3$, $R_3Al$ and $R_2Zn$ wherein R is $C_1$-$C_{20}$ alkyl and X is Cl or Br, the oligomerization being conducted in a reactor vessel at 50° C. to 300° C. at a pressure of about 15 to 5000 psig in the liquid phase, with the presence of water in the reactor vessel being minimized such that the ratio of moles of zirconium to moles of water is at least 10 to 1.

2. The process of claim 1 wherein the amount of said zirconium adduct is about $1 \times 10^{-6}$ to $200 \times 10^{-6}$ moles per gram of olefin being oligomerized.

3. The process of claim 2 wherein the molar ratio of said alkyl metal catalyst to said zirconium adduct is about 15:1 to 3:1.

4. The process of claim 1 wherein the olefin is a $C_3$-$C_{20}$ linear aliphatic hydrocarbyl monounsaturated olefin.

5. The process of claims 1, 2, 3 or 4 wherein said organic compound is an ester of the formula $R_1COOR_2$ wherein $R_1$ and $R_2$ represent alkyl, aryl, alkaryl or aralkyl groups having a total of 1 to 30 carbon atoms and $R_1$ may be also H.

6. The process of claim 5 wherein said organic compound is an acetate ester of the formula $CH_3COOR_1$ where $R_1$ has about 6 to 16 carbon atoms and the adduct is of the formula $(ZrCl_4 \cdot CH_3COOR_1)_2$.

7. The process of claims 1, 2, 3 or 4 wherein said adduct is an adduct of $ZrCl_4$.

8. The process of claim 6 wherein the acetate ester is a mixture of isomers of isodecyl acetate.

9. The process of claim 1 wherein said ketones have the formula $R_1C(:O)R_2$ where $R_1$ and $R_2$ represent alkyl, aryl, alkaryl or aralkyl groups having a total of 1 to 30 carbon atoms or a cyclo aliphatic hydrocarbyl group having 4 to 16 carbon atoms.

10. The process of claim 1 wherein said ethers have the formula $R_1OR_2$ where $R_1$ and $R_2$ represent alkyl, aryl, alkaryl and aralkyl groups having a total of 1 to 30 carbon atoms or a cyclo aliphatic hydrocarbyl group having 4 to 16 carbon atoms.

11. The process of claim 1 wherein said aldehydes have the formula $R_1C(:O)H$ where $R_1$ represents alkyl, aryl, alkaryl and aralkyl groups having 1 to 30 carbon atoms.

12. The process of claim 1 wherein said nitriles have the formula $RC\equiv N$ wherein R represents alkyl, aryl, alkaryl and aralkyl groups having a total of 1 to 30 carbon atoms.

13. The process of claim 1 wherein said anhydrides have the formula $(R-C(:O))_2O$ wherein R represents alkyl, aryl, alkaryl and aralkyl groups having a total of 1 to 30 carbon atoms.

14. The process of claim 1 wherein said acid chlorides have the formula $RC(:O)Cl$ where R represents alkyl, aryl, alkaryl and aralkyl groups having a total of 1 to 30 carbon atoms.

15. The process of claim 1 wherein said amides have the formulas $RC(:O)NH_2$, $RC(:O)NHR$ and $RC(:O)NR_2$ where R represents alkyl, aryl, alkaryl and aralkyl groups having a total of 1 to 30 atoms.

16. The process of claims 1, 2, 3 or 4 wherein the olefin is propylene.

17. The process of claims 1, 2, 3 or 4 wherein there is present a solvent which comprises p-xylene, mixed xylenes, or n-decane.

18. The process of claims 1, 2, 3 or 4 wherein the alkyl metal catalyst is diethylaluminum chloride, aluminum ethyl dichloride or mixtures thereof.

19. The process of claims 1, 2, 3 or 4 wherein the olefin is 1-decene.

* * * * *